US012415072B2

(12) United States Patent
Colachis et al.

(10) Patent No.: US 12,415,072 B2
(45) Date of Patent: Sep. 16, 2025

(54) SPASTICITY TREATMENT DEVICE AND METHOD

(71) Applicant: Battelle Memorial Institute, Columbus, OH (US)

(72) Inventors: Samuel Colachis, Columbus, OH (US); Michael Darrow, Missouri City, TX (US); Eric C. Meyers, Columbus, OH (US); Lauren Wengerd, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 322 days.

(21) Appl. No.: 17/965,279

(22) Filed: Oct. 13, 2022

(65) Prior Publication Data
US 2023/0124842 A1 Apr. 20, 2023

Related U.S. Application Data

(60) Provisional application No. 63/256,375, filed on Oct. 15, 2021.

(51) Int. Cl.
*A61N 1/36* (2006.01)
*A61B 5/00* (2006.01)
*A61B 5/256* (2021.01)
*A61B 5/296* (2021.01)
*A61B 5/395* (2021.01)
*A61N 1/04* (2006.01)

(52) U.S. Cl.
CPC .......... *A61N 1/36003* (2013.01); *A61B 5/256* (2021.01); *A61B 5/296* (2021.01); *A61B 5/395* (2021.01); *A61B 5/4836* (2013.01); *A61B 5/6804* (2013.01); *A61B 5/7425* (2013.01); *A61N 1/0452* (2013.01); *A61N 1/0456* (2013.01); *A61N 1/0484* (2013.01); *A61B 2562/046* (2013.01)

(58) Field of Classification Search
CPC ...... A61N 1/36003; A61B 5/395; A61B 5/296
USPC .......................................................... 607/48
See application file for complete search history.

(56) References Cited

U.S. PATENT DOCUMENTS

2006/0247733 A1* 11/2006 Amer ...................... A41D 1/00
607/148
2022/0386935 A1* 12/2022 Lo ..................... A61N 1/36031

\* cited by examiner

*Primary Examiner* — Nadia A Mahmood
(74) *Attorney, Agent, or Firm* — Lippes Mathias LLP

(57) ABSTRACT

A method of treating spasticity uses a garment worn on a target anatomy so as to arrange electrodes on an inner surface of the garment contacting the skin of the target anatomy. Using an electronic processor, a spasticity treatment cycle is performed. The spasticity treatment cycle is initiated by providing a human-perceptible prompt to initiate a spastic event, or by triggering the spastic event by applying electrical stimulation to at least a portion of the target anatomy using the electrodes. Thereafter, electromyography (EMG) signals are measured from the target anatomy using the electrodes. One or more spasm regions in the target anatomy are identified based on the EMG signals. Targeted treatment of the one or more spasm regions is performed using neuromuscular electrical stimulation (NMES), or is directed to be performed by displaying a representation of the target anatomy with the one or more spasm regions indicated on the representation.

20 Claims, 2 Drawing Sheets

SPASTICITY TREATMENT DEVICE AND METHOD

This application claims the benefit of U.S. Provisional Application No. 63/256,375 filed Oct. 15, 2021 and titled "SPASTICITY TREATMENT DEVICE AND METHOD", which is incorporated herein by reference in its entirety.

BACKGROUND

The following relates to the neurological injury rehabilitation arts, to methods and apparatuses for aiding stroke recovery, methods and apparatuses for aiding spinal cord injury recovery, and to the like.

Stroke often results in significant reduction of motor control and can present with many symptoms including spasticity. Spasticity is a condition in which the muscles involuntarily tighten, thus preventing normal movement and possibly passive range of motion. Having limited passive range of motion can prohibit many aspects of rehabilitation including more advanced techniques like functional electrical stimulation (FES).

BRIEF SUMMARY

In accordance with some illustrative embodiments disclosed herein, a method of treating spasticity is disclosed. The method includes: measuring electromyography (EMG) signals from a target anatomy using electrodes contacting skin of the target anatomy; identifying one or more spasm regions of the target anatomy based on the EMG signals; and at least one of (i) displaying a representation of the target anatomy with the one or more spasm regions indicated on the representation, and/or (ii) applying neuromuscular electrical stimulation (NMES) to the one or more spasm regions in the target anatomy using the electrodes contacting the skin of the target anatomy.

In accordance with some illustrative embodiments disclosed herein, a device for treating spasticity is disclosed. The device includes a garment configured to be worn on a target anatomy, electrodes arranged on an inner surface of a garment so as to contact skin of the target anatomy when the garment is worn on the target anatomy, and an electronic processor. The electronic processor is programmed to perform a spasticity treatment cycle including: measuring EMG signals from the target anatomy using the electrodes; identifying one or more spasm regions in the target anatomy based on the measured EMG signals; and at least one of (i) displaying a representation of the target anatomy on a display of the electronic processor with the one or more spasm regions indicated on the representation, and/or (ii) applying NMES to the one or more spasm regions in the target anatomy using the electrodes.

In accordance with some illustrative embodiments disclosed herein, a method of treating spasticity is disclosed. The method includes donning a garment on a target anatomy whereby electrodes arranged on an inner surface of the garment contact the skin of the target anatomy, and, using an electronic processor, performing a spasticity treatment cycle, The spasticity treatment cycle includes: initiating the spasticity treatment cycle by providing a human-perceptible prompt to initiate a spastic event or by triggering a spastic event by applying electrical stimulation to at least a portion of the target anatomy using the electrodes; following the initiating, measuring electromyography (EMG) signals from the target anatomy using the electrodes; identifying one or more spasm regions in the target anatomy based on the EMG signals; and performing or directing performance of targeted treatment of the identified one or more spasm regions.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

DETAILED DESCRIPTION

In embodiments disclosed herein, electromyography (EMG) is used in a spasticity treatment process that (1) stimulates a spastic event, (2) detects local regions of spasticity (i.e., spasm regions) and (3) provides targeted treatment to those local regions of spasticity. In some embodiments, the EMG is measured using a high density array of electrodes, i.e. HD-EMG. The electrodes may be conveniently disposed in a sleeve or other garment sized and shaped to be worn on the arm, leg, or other anatomy to be treated.

In some embodiments, neuromuscular electrical stimulation (NMES) is used at a low frequency (8-40 Hz in some nonlimiting illustrative embodiments) to treat muscles detected to produce spasticity in response to the stimulated spastic event, thereby temporarily reducing spasticity and allowing for full passive range of motion. The disclosed approaches advantageously apply NMES specifically to the muscles detected as exhibiting spasticity. The approach is suitable for automated or semi-automated use without clinical oversight to identify musculature with spasticity.

Figure 1:
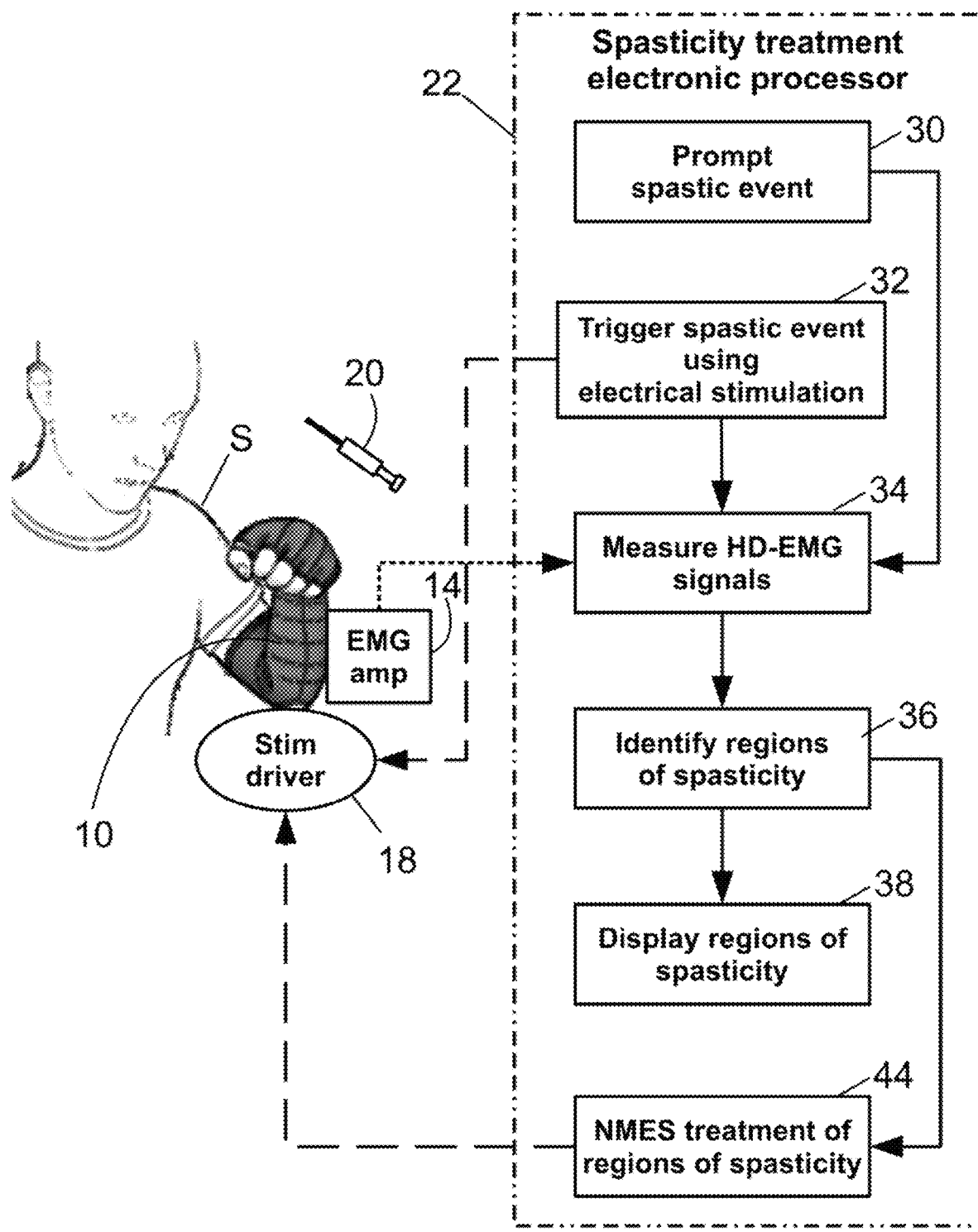
FIGS. 1 and 2 show alternative diagrammatic views of a system for providing targeted therapy to treat spasticity.
Figure 2:
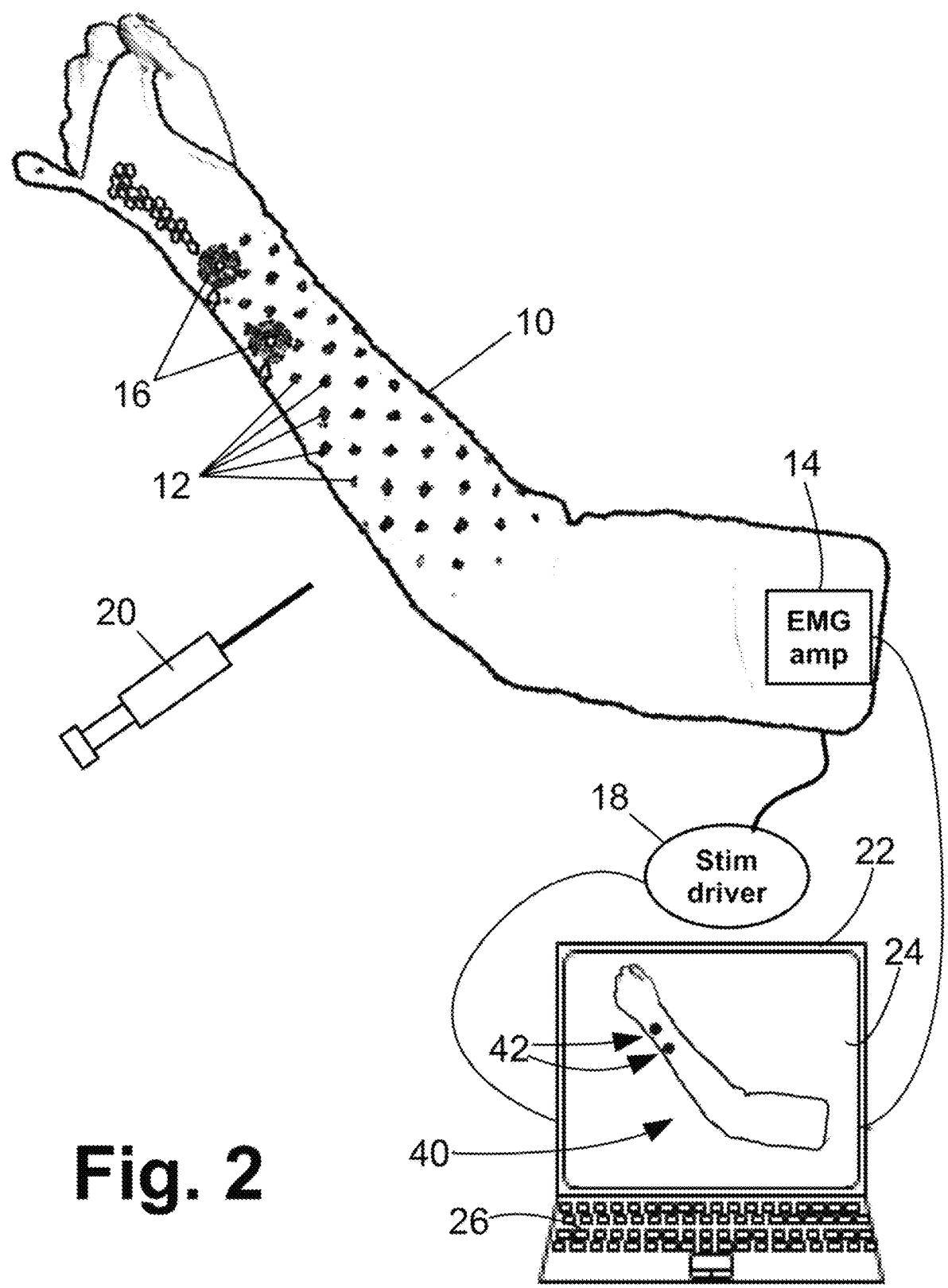

With reference to FIGS. 1 and 2, in an illustrative embodiment a spasticity reduction garment 10, such as an illustrative sleeve 10, is worn on the forearm (or other target anatomy to be treated) of a subject S (e.g., a patient, rehabilitation subject, or so forth). As best seen in FIG. 2, the sleeve 10 includes electrodes 12 distributed over the surface of the arm (or, more generally, over the surface of a target anatomy such as an arm, leg, torso, or other anatomy suffering from spasticity). It should be noted that the electrodes 12 are diagrammatically shown in FIG. 2—in practice, the electrodes 12 are arranged on an inner surface of the sleeve 10 so as to contact the skin of the target anatomy when the garment 10 is donned on the target anatomy. (The inner surface of the garment 10 is the surface of the garment 10 that faces toward the skin of the anatomy, e.g. illustrative arm, when the garment 10 is worn on the anatomy). More generally, the electrodes 12 are arranged on an inner surface of a garment 10 to contact skin of the target anatomy when the garment 10 is worn on the target anatomy. Use of the illustrative sleeve or other garment 10 that is worn on the target anatomy is a convenient way to quickly position a large number of electrodes 12 distributed over the skin of the target anatomy. However, it is contemplated to apply the electrodes to the skin using another approach, such as applying individual transcutaneous electrodes to the skin using electrically conductive adhesive to adhere the individual electrodes to the skin.

A multichannel EMG amplifier 14 is operatively connected to the electrodes 12 to read the EMG signals. The garment 10 preferably includes a sufficient number of electrodes to provide suitable spatial resolution for detecting regions of spasticity (i.e., spasm regions). For example, in some nonlimiting illustrative embodiments, the garment 10 includes at least 100 electrodes distributed over the surface of the arm or other target anatomy when the garment is worn on the target anatomy. This enables high-density EMG (HD-EMG) measurements, e.g. capable of precisely identifying regions of spasticity. Notably, since spasticity is a condition in which the muscles involuntarily tighten, such muscle tightening generates EMG signals that can be detected by the electrodes 12. FIG. 2 diagrammatically indicates two representative spasm regions 16. A spasm region is a local area of the target anatomy that is experiencing a spasm or rapid sequence of spasms. In some cases, a spasm region may correspond to a particular muscle or muscle group that experiences spasms. In some cases, a spasm region may correspond to a neuromuscular motor unit controlled by a specific nerve. These are merely illustrative examples.

The multichannel EMG amplifier 14 may have a separate channel for each electrode 12 so that the number of channels of the EMG amplifier 14 equals the number of electrodes 12. Alternatively, to reduce hardware costs, the EMG amplifier 14 may use time-dimension multiplexing (TDM) to enable each channel of the EMG amplifier 14 to read multiple electrodes 12. Because the EMG signals are of low intensity, in some embodiments the EMG amplifier 14 (or at least a front-end amplifier circuit portion thereof) may be integrated with the sleeve or other garment 10 as diagrammatically shown in FIG. 2 to reduce the signal path lengths from the electrodes to the EMG amplifier 14.

In embodiments in which neuromuscular electrical stimulation (NMES) is used to treat the detected spasm regions, a stimulation driver 18 is also coupled with the electrodes 12 to apply targeted electrical stimulation to detected spasm regions.

Rather than (or in addition to) treating detected spasticity with NMES targeted to the detected region(s) of spasticity, the targeted spasticity treatment may include delivering an injection of botulinum A (e.g., Botox®), botulinum B, or another botulinum toxin, or another spasticity-suppression pharmacological agent such as phenol/alcohol, to the detected spastic region(s) using a hypodermic needle 20 or the like. In some embodiments, the stimulation driver 18 may be used to deliver electrical stimulation to induce muscle contractions so as to trigger a spastic event using the electrical stimulation.

The system further includes a spasticity treatment electronic processor 22. In the diagrammatic representation of FIG. 1 this processor 22 is shown as a diagrammatic functional representation, while in FIG. 2 the spasticity treatment electronic processor 22 is shown as an illustrative implementation as a computer 22 having an optional display 24 and an optional keyboard and/or other user input device 26. More generally, the spasticity treatment electronic processor 22 may comprise a notebook computer, desktop computer, a mobile device such as a cellular telephone (cellphone) or tablet computer, or so forth, that is operatively connected to read EMG signals from the EMG amplifier 14 and to control the optional NMES driver 18.

With particular reference to FIG. 1, one spasticity treatment cycle of a spasticity treatment method is diagrammatically shown. The spasticity treatment cycle is performed by the spasticity treatment electronic processor 22. To this end, the spasticity treatment electronic processor 22 is programmed by instructions stored on a non-transitory storage medium (not shown) and readable and executable by the spasticity treatment electronic processor 22 to perform the spasticity treatment cycle. In some embodiments, the electronic processor 22 is further programmed to perform autonomous repetitions of the spasticity treatment cycle without human intervention. The non-transitory storage medium may, for example, comprise a hard drive or other magnetic storage medium, a flash memory, solid state drive (SSD) or other electronic memory, an optical disk or other optical memory, various combinations thereof, and/or so forth.

As diagrammatically shown in FIG. 1, a spasticity treatment cycle is initiated in an operation 30 by providing a human-perceptible prompt to initiate a spastic event. For example, the operation 30 may display an instruction on the display 24 asking a nurse or other assistant, or for the person S undergoing treatment, to perform an action to initiate a spastic event. The requested action may vary depending on the availability of an assistant, the target anatomy suffering occasional spasms, the type(s) of movement of that anatomy that typically trigger spasms, whether volitional control of the target anatomy is partially disabled (for example, as a consequence of a stroke or spinal cord injury), and/or so forth. As an example, if the subject S typically experiences spasms when clenching his or her fist, then the operation 30 may instruct the subject S to perform a fist clench. As another example, if the subject S typically experiences spasms when lifting a leg (where in this example the target anatomy is said leg), then the operation 30 may instruct the subject S to lift the leg. If the target anatomy is partially disabled then the operation 30 may instruct an assistant to manipulate the target anatomy of the subject S in a way that typically evokes a spastic response.

In some alternative embodiments, the spasticity treatment cycle is initiated in an alternative operation 32 by applying electrical stimulation to at least a portion of the target anatomy using the electrodes 12 of the sleeve or other garment 10 and the stimulation amplifier 18. For example, electrical stimulation of sufficient amplitude to induce functional electrical stimulation (FES) in which the stimulation induces muscle contractions can be used to trigger a spastic event using the FES. In another embodiment, a lower amplitude of electrical stimulation can be applied to induce the spasms, such as may be sufficient to induce neuromuscular electrical stimulation (NMES) but not sufficient to produce a functional response (i.e. movement).

After initiating the spasticity treatment cycle by way of operation 30 or operation 32, in an operation 34 electromyography (EMG) signals from a target anatomy are measured using the electrodes 12 contacting skin of the target anatomy and the EMG amplifier 14. In an operation 36, spasm regions 16 (see FIG. 2) are identified based on the EMG signals. As previously noted, a spasm is a condition in which muscles involuntarily tighten. Consequently, a spasm generates EMG signals that can be detected by the electrodes 12. The EMG signals will generally only be present in the spasm region, or at least will only be present at above some threshold amplitude in the spasm region. Hence, in some embodiments the operation 36 identifies the one or more spasm regions 16 as one or more contiguous regions within which the EMG signals exceed a threshold amplitude. Additionally or alternatively, other spatially varying characteristics of the EMG signals can be used to identify the one or more spasm regions 16. For example, if the involuntary muscle contractions constituting the spasm occur in a specific frequency range, then the operation 36 may identify the one or more spasm regions 16 as contiguous regions in which the EMG signals vary at that frequency range. The appropriate threshold amplitude, frequency range, or other EMG signal characteristics used in the operation 36 for identifying the one or more spasm regions 16 can be calibrated empirically for the subject S specifically. Alternatively, if the subject S is experiencing spasms of a particular type or class of spasms, then the appropriate threshold amplitude, frequency range, or other EMG signal characteristics for identifying a spasm region can be calibrated empirically for historical subjects suffering from that type or class of spasms. In some embodiments, the operation 36 employs machine learning (ML), for example an artificial neural network (ANN), to identify the spasm regions 16. The ANN or other ML component is suitably trained on representative EMG data that includes manually labeled spastic events to decode (i.e. identify) regions of spasticity across the array of electrodes.

With the spasm regions identified, targeted treatment of the identified one or more spasm regions 16 can be performed or directed to be performed. In one example, in an operation 38 a representation 40 (see FIG. 2) of the target anatomy is displayed, for example on the display 24 of the electronic processor 22, with the one or more spasm regions indicated on the representation, for example as markers or graphically delineated regions 42 (see FIG. 2). In a variant (and not necessarily mutually exclusive) embodiment, the one or more spasm regions can be indicated directly on the sleeve or other garment 10, for example by activating light emitting diodes (LEDs) disposed on the exterior of the sleeve or other garment 10. In this variant, the LED or LEDs on the sleeve 10 at the location(s) of the spasm region(s) 16 are suitably activated to light up to directly indicate the spasm regions. Optionally, the operation 38 may also provide additional information. For example, the amplitude of the EMG signals in the spasm region(s) 16 can be displayed (or indicated by the brightness of the LED illumination in embodiments employing LEDs on the exterior of the sleeve 10), optionally with scaling, to provide a qualitative metric of the strength of the spasms. In a variant embodiment, if accelerometers or other inertial measurement units (IMUs) are integrated into the garment 10, then these can be used to quantitatively measure the muscle spasms in terms of physical movement caused by the involuntary spastic contractions. In this case, a scaling transform can be empirically generated to enable converting the EMG amplitude to a quantitative spasm strength measurement.

The graphical representation 40 advantageously informs a nurse or other assistant, or the person S undergoing treatment if qualified, precisely where to administer the treatment to effectively treat the spasms. In one approach, the assistant can deliver one or more injections of a spasticity-suppression pharmacological agent to the detected one or more spasm regions 16 using the illustrative hypodermic needle 20. In some embodiments, the sleeve 10 comprises a fabric material, for example an elastane fabric such as spandex or lycra, and/or has an array of small openings large enough to admit a hypodermic needle, and in such embodiments the injection may be applied directly through the fabric or a proximate opening so that the pharmacological agent can be administered while the sleeve 10 is worn. In doing so, the assistant is conveniently guided by the graphically delineated spasm regions 42 superimposed on the representation 40 of the target anatomy. In the aforementioned variant embodiment in which the spasm region(s) are directly indicated on the sleeve or other garment 10 by activation of one or more LEDs disposed on the outer surface of the sleeve 10, the assistant can directly inject the pharmacological agent through the sleeve (or a proximate opening of an array of openings of the sleeve) in the region indicated by the activated LED(s). In some embodiments, the spasticity-suppression pharmacological agent may comprise a botulinum toxin such as botulinum A (e.g., Botox®), botulinum B, or another botulinum toxin. In other embodiments, the spasticity-suppression pharmacological agent may comprise a phenol/alcohol agent. These are merely illustrative examples. Moreover, targeted non-pharmacological treatments are contemplated, such as applying force at the spasm regions 16.

In other embodiments, the targeted treatment of the identified one or more spasm regions 16 can be performed autonomously without human intervention in an operation 44 by way of applying neuromuscular electrical stimulation (NMES) to the one or more spasm regions 16 in the target anatomy using the electrodes 12 contacting skin of the target anatomy and the stimulation amplifier 18. For example, a low frequency NMES, applied with a frequency of 8-40 Hz in some non-limiting illustrative embodiments, is expected to suppress spasms in the identified one or more spasm regions 16.

It is also noted that the operations 38 and 44 are not necessarily mutually exclusive. For example, both operations can be performed so that the nurse or other assistance is informed of the location(s) of the spasm regions 16 via operation 38 and NMES treatment is also performed via operation 44. In such a combination, the information provided in the operation 38 may be recorded to keep track of where spasms are occurring (and their qualitative or quantitative strength, if displayed), and/or the graphically delineated spasm regions 42 may be used to guide in additional treatment beyond the NMES (e.g. a Botox® injection).

In some more particular embodiments, the spasticity treatment cycle is initiated autonomously without human intervention in the operation 32 by applying electrical stimulation, and the targeted treatment is also delivered autonomously without human intervention in the operation 44. In this case, the entire spasticity treatment cycle can be performed autonomously without human intervention. In such embodiments, the electronic processor 22 may optionally be programmed to perform autonomous repetitions of the spasticity treatment cycle without human intervention. The repetitions may be performed at various intervals, e.g. every 5 minutes in one non-limiting illustrative example. In another approach, the subject S can trigger a repetition of the autonomous spasticity treatment cycle manually, for example by pressing a button (not shown) on the garment 10.

In some embodiments, the spasticity treatment electronic processor 22 may be programmed to quantify effectiveness of the spasticity treatment. In such embodiments, the treatment is applied, for example by way of one or more injections of a spasticity-suppression pharmacological agent to the spasm region(s), by applying NMES to the spasm region(s) using the electrodes 12, or a combination thereof. After the treatment, the spastic event is induced to occur again by a repetition of the operation 32, and the EMG activity then remeasured by a repetition of the operation 34. The post-treatment EMG activity thusly measured is compared with the EMG activity that was measured pre-treatment, and the reduction in spasticity (if any) is quantified. In one approach, this quantification can comprise quantifying the number of detected spastic events post-treatment versus pre-treatment. This comparison could be performed by a trained clinician visually observing the graphically delineated regions 42 (see FIG. 2), or in the variant embodiment visually observing the activated LED(s) on the exterior of the sleeve 10 that are activated to indicate the spasm region(s). Additionally or alternatively, the quantitative comparison can be performed by statistical methods.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method of treating spasticity, the method comprising:
measuring electromyography (EMG) signals from a target anatomy using electrodes contacting skin of the target anatomy;
identifying one or more spasm regions of the target anatomy based on the EMG signals;
displaying a representation of the target anatomy with the one or more spasm regions indicated on the representation; and
after displaying the representation of the target anatomy, delivering one or more injections of a spasticity-suppression pharmacological agent to the detected one or more spasm regions using a hypodermic needle.

2. The method of claim 1 wherein the electrodes are arranged on an inner surface of a garment and the method further comprises:
donning the garment on the target anatomy whereby the electrodes arranged on the inner surface of the garment contact the skin of the target anatomy.

3. The method of claim 1 wherein the one or more spasm regions are identified as one or more contiguous regions within which the EMG signals exceed a threshold amplitude.

4. The method of claim 1 further comprising:
prior to the measuring of the EMG signals, providing a human-perceptible prompt to initiate a spastic event.

5. The method of claim 1 further comprising:
prior to the measuring of the EMG signals, triggering a spastic event by applying electrical stimulation to at least a portion of the target anatomy using the electrodes contacting skin of the target anatomy.

6. The method of claim 1 wherein the method includes applying NMES to the one or more spasm regions in the target anatomy using the electrodes contacting skin of the target anatomy.

7. The method of claim 6 wherein the NMES has a frequency of 8-40 Hz.

8. A device for treating spasticity, the device comprising:
a garment configured to be worn on a target anatomy;
electrodes arranged on an inner surface of a garment so as to contact skin of the target anatomy when the garment is worn on the target anatomy; and
an electronic processor programmed to perform a spasticity treatment cycle including:
measuring electromyography (EMG) signals from the target anatomy using the electrodes;
prior to the measuring of the EMG signals, initiating a spastic event by providing a human-perceptible prompt to initiate the spastic event or triggering the spastic event by applying electrical stimulation to at least a portion of the target anatomy using the electrodes arranged on the inner surface of the garment;
identifying one or more spasm regions in the target anatomy based on the measured EMG signals; and
at least one of (i) displaying a representation of the target anatomy on a display of the electronic processor with the one or more spasm regions indicated on the representation, and/or (ii) applying neuromuscular electrical stimulation (NMES) to the one or more spasm regions in the target anatomy using the electrodes.

9. The device of claim 8 wherein the electrodes include at least 100 electrodes arranged on the inner surface of the garment so as to contact the skin of the target anatomy when the garment is worn on the target anatomy.

10. The device of claim 8 wherein the electronic processor is programmed to identify the one or more spasm regions in the target anatomy as one or more contiguous regions within which the EMG signals exceed a threshold amplitude.

11. The device of claim 8 wherein the spasticity treatment cycle includes, prior to the measuring of the EMG signals, providing the human-perceptible prompt to initiate a spastic event.

12. The device of claim 8 wherein the spasticity treatment cycle includes, prior to the measuring of the EMG signals, triggering a spastic event by applying electrical stimulation to at least a portion of the target anatomy using the electrodes arranged on the inner surface of the garment.

13. The device of claim 8 wherein the spasticity treatment cycle includes displaying a representation of the target anatomy with the one or more spasm regions indicated on the representation.

14. The device of claim 8 wherein the spasticity treatment cycle includes applying NMES to the one or more spasm regions in the target anatomy using the electrodes arranged on the inner surface of the garment.

15. The device of claim 14 wherein:
the spasticity treatment cycle further includes, prior to the measuring of the EMG signals, triggering a spastic event by applying electrical stimulation to at least a portion of the target anatomy using the electrodes arranged on the inner surface of the garment; and
the electronic processor is further programmed to perform autonomous repetitions of the spasticity treatment cycle without human intervention.

16. A method of treating spasticity, the method comprising:
donning a garment on a target anatomy whereby electrodes arranged on an inner surface of the garment contact the skin of the target anatomy; and
using an electronic processor, performing a spasticity treatment cycle including:
initiating a spastic event by providing a human-perceptible prompt to initiate the spastic event or by triggering the spastic event by applying electrical stimulation to at least a portion of the target anatomy using the electrodes;
following the initiating, measuring electromyography (EMG) signals from the target anatomy using the electrodes;
identifying one or more spasm regions in the target anatomy based on the EMG signals; and
performing or directing performance of targeted treatment of the identified one or more spasm regions.

17. The method of claim 16 wherein the performing or directing performance of the targeted treatment includes:
directing performance of the targeted treatment by displaying a representation of the target anatomy with the one or more spasm regions indicated on the representation.

18. The method of claim 17 wherein the performing or directing performance of the targeted treatment includes:

performing the targeted treatment by applying neuromuscular electrical stimulation (NMES) to the one or more spasm regions in the target anatomy using the electrodes.

19. The method of claim 16 wherein the initiating comprises initiating the spastic event by providing the human-perceptible prompt to initiate the spastic event.

20. The method of claim 16 wherein the initiating comprises triggering the spastic event by applying electrical stimulation to at least a portion of the target anatomy using the electrodes.

* * * * *